United States Patent [19]

Holton et al.

[11] Patent Number: 5,654,447

[45] Date of Patent: Aug. 5, 1997

[54] PROCESS FOR THE PREPARATION OF 10-DESACETOXYBACCATIN III

[75] Inventors: Robert A. Holton, Tallahassee, Fla.; Carmen Somoza, Corvallis, Oreg.

[73] Assignee: Florida State University, Tallahassee, Fla.

[21] Appl. No.: 500,868

[22] PCT Filed: Jan. 14, 1994

[86] PCT No.: PCT/US94/00499

§ 371 Date: Sep. 22, 1995

§ 102(e) Date: Sep. 22, 1995

[87] PCT Pub. No.: WO94/15929

PCT Pub. Date: Jul. 21, 1994

Related U.S. Application Data

[63] Continuation-in-part of Ser. No. 94,545, Jul. 20, 1993, which is a continuation-in-part of Ser. No. 5,229, Jan. 15, 1993, Pat. No. 5,338,872, and Ser. No. 34,247, Mar. 22, 1993, Pat. No. 5,430,160, which is a continuation-in-part of Ser. No. 949,107, Sep. 22, 1992, abandoned, which is a continuation-in-part of Ser. No. 863,849, Apr. 6, 1992, abandoned, which is a continuation-in-part of Ser. No. 862,955, Apr. 3, 1992, abandoned, which is a continuation-in-part of Ser. No. 763,805, Sep. 23, 1991, abandoned.

[51] Int. Cl.$^6$ .................................................. C07C 305/14
[52] U.S. Cl. .................................................. 549/510
[58] Field of Search .................................................. 549/510

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,924,012 | 5/1990 | Colin et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 549/511 |
| 5,136,060 | 8/1992 | Holton | 549/510 |
| 5,175,315 | 12/1992 | Holton | 549/510 |
| 5,200,534 | 4/1993 | Rao | 549/510 |
| 5,243,045 | 9/1993 | Holton et al. | 544/60 |
| 5,248,796 | 9/1993 | Chen et al. | 549/510 |
| 5,250,683 | 10/1993 | Holton et al. | 544/60 |
| 5,254,580 | 10/1993 | Chen et al. | 514/449 |
| 5,254,703 | 10/1993 | Holton | 549/510 |
| 5,264,591 | 11/1993 | Bombardelli et al. | 549/214 |
| 5,272,171 | 12/1993 | Ueda et al. | 514/449 |
| 5,277,400 | 1/1994 | Holton et al. | 514/444 |
| 5,294,637 | 3/1994 | Chen et al. | 514/449 |
| 5,299,526 | 4/1994 | Holton | 549/213 |
| 5,336,785 | 8/1994 | Holton | 549/214 |
| 5,338,872 | 8/1994 | Holton et al. | 549/510 |
| 5,350,866 | 9/1994 | Holton et al. | 549/510 |
| 5,384,399 | 1/1995 | Holton | 544/97 |
| 5,399,726 | 3/1995 | Holton et al. | 549/510 |
| 5,405,972 | 4/1995 | Holton et al. | 549/214 |
| 5,430,160 | 7/1995 | Holton | 549/510 |

FOREIGN PATENT DOCUMENTS

| | | |
|---|---|---|
| 0 247 378 | 4/1987 | European Pat. Off. . |
| 0 253 738 | 7/1987 | European Pat. Off. . |
| 0 253 739 | 7/1987 | European Pat. Off. . |
| 0 336 840 | 4/1989 | European Pat. Off. . |
| 0 336 841 | 4/1989 | European Pat. Off. . |
| 0 400 971 | 5/1990 | European Pat. Off. . |
| 0 428 376 | 11/1990 | European Pat. Off. . |
| 0 534 707 | 9/1992 | European Pat. Off. . |
| 0 534 708 | 9/1992 | European Pat. Off. . |
| 0 534 709 | 9/1992 | European Pat. Off. . |
| 91/9244 | 11/1991 | South Africa . |
| WO92/09589 | 11/1991 | WIPO . |
| WO93/02065 | 7/1992 | WIPO . |

OTHER PUBLICATIONS

Bartholomew et al. "A Novel Rarrangement Reaction Conversion of 3-(chloromethyl)azetidin-2-ones to Azetidine-3-carboxylic Acid Esters", Tetrahedron Letters, vol. 32, No. 36, pp. 4795–4798 (1991).

Borman "New Family of Taxol, Taxotere Analogs Developed" Science & Technology, Chem. & Eng. News, pp. 36–37 (Apr. 12, 1993).

Chaudhary et al. "Synthesis of 10–Deacetoxytaxol and 10–Deoxytaxotere" Tetrahedron Letters, vol. 34, No. 31, pp. 4921–4924 (1993).

Chen et al. "Taxol Structure–Activity Relationships: Synthesis and Biological Evaluation of 2–Deoxytaxol" Tetrahedron Letters, vol. 34, No. 20, pp. 3205–3206 (1993).

Denis et al. "A Highly Efficient, Practical Approach to Natural Taxol" Journal of American Chemical Society, vol. 110, No. 17, pp. 5917–5919 (1988).

Farina et al. "The Chemistry of Taxanes: Unexpected Rearangement of Baccatin III During Chemoselective Debenzoylation with $Bu_3SnOMe/LiCl$" Tetrahedron Letters, vol. 33, No. 28 pp. 3979–3982 (1992).

Hanessian et al. "A Practical Synthesis of 2–Deoxy Aldonolacetones via a $SmI_2$–Mediated α–Deoxygenation Reaction" Tetrahedron Letters, vol. 33, No. 5, pp. 573–576 (1992).

Holton "Synthesis of the Taxane Ring System" Journal of the American Chemical Soc., vol. 106, pp. 5731–5732 (1984).

(List continued on next page.)

Primary Examiner—James H. Reamer
Attorney, Agent, or Firm—Senniger, Powers, Leavitt & Roedel

[57] ABSTRACT

A process for abstracting a C10 hydroxy, acyloxy or sulfonyloxy substituent from a taxane in which the C10 hydroxy, acyloxy or sulfonyloxy substituted taxane is reacted with samarium diiodide.

9 Claims, No Drawings

OTHER PUBLICATIONS

Holton et al. "A Synthesis of Taxusin" Journal of American Chemical Soc., vol. 110, pp. 6558–6560 (1988).

Holton et al. "A Novel Lanthanide–Induced Rearrangement" Journal of Organic Chemistry, vol. 53, No. 25, pp. 5981–5983 (1988).

Inanaga et al. "$SmI_2$–Promoted Deacetoxylation of O–Acetylsugar Lactones. An Easy Access to Deoxysugar Lactones" Chemical Letters, pp. 1025–1026 (1991).

Kaiser et al. "Synthesis of Esters of Acid–Unstable Alcohols by Means of n–butyllithium" Journal of Organic Chemistry, vol. 35, p. 1198 (1970).

Kingston et al. "Progress in the Chemistry of Organic Natural Products" Springer–Verlag, New York (1993) pp. 1–206.

Klein "Synthesis of 9–Dihydrotaxol: A Novel Bioactive Taxane" Tetrahedron Letters, vol. 34, No. 13, pp. 2047–2050 (1993).

Kusuda et al. "A Highly Effective Deoxygenation of α–oxygenated Esters Via $SmI_2$–Induced Electron Transfer Process" Tetrahedron Letters, vol. 30, No. 22, pp. 2945–2948 (1989).

Magri et al. "Modified Taxols, 4. Synthesis and Biological Activity of Taxols Modified in the Side Chain" Journal of Natural Products, vol. 51, No. 2, pp. 298–306 (1988).

Miller et al. "Antileukemic Alkaloids from Taxus Wallichiana Zucc." Journal of Organic Chemistry, vol. 46, No. 7, pp. 1469–1474 (1981).

Molander et al. "Lanthanides in Organic Synthesis. 2. Reduction of α–Heterosubstituted Ketones" Journal of Organic Chemistry, vol. 51, No. 7, pp. 1135–1138 (1986).

Mukerjee et al. "β–Lactams: Retrospect and Prospect" Tetrahedron Letters, vol. 34, No. 52, pp. 1731–1767 (1978).

Ojima et al. "New and Efficient Approaches to the Semisynthesis of Taxol and its C–13 Side Chain Analogs by Means of β–Lactam Synthon Method" Tetrahedron Letters, vol. 48, No. 34, pp. 6985–7012 (1992).

Samaranayake et al. "Modified Taxols. 5.1 Reaction of Taxol with Electrophilic Reagents and Preparation of a Rearranged Taxol Derivative with Tubulin Assembly Activity3" Journal of Organic Chemistry, vol. 56, No. 17, pp. 5114–5119 (1991).

Schulz et al. "Synthesis of New N–radicals of Tetrazan––1–yl" Chemical Abstracts, vol. 108, No. 37298C, p. 581 (1988).

Senilh et al. "Hemisynthese de nouveaux analogs du taxol. Etude de leur interaction avec la tubuline" C.R. Acad. Soc. Paris, Serie II, vol. 229, No. 15, pp. 1039–1043, (Nov. 1984).

Wani et al. "Plant Antitumor Agents. VI. The Isolation and Structure of Taxol, a Novel Antileukemic and Antitumor Agent from Taxus brevifolia" Journal of American Chemical Soc., vol. 93, No. 9, pp. 2325–2327 (1971).

Witherup et al. "High Performance Liquid Chromatographic Separation of Taxol and Related Compounds From Taxus Brevifolia" Journal of Liquid Chromatography, vol. 12, No. 11, pp. 2117–2132 (1989).

PROCESS FOR THE PREPARATION OF 10-DESACETOXYBACCATIN III

REFERENCE TO RELATED APPLICATIONS

This application is a continuation-in-part of U.S. application Ser. No. 08/094,545, filed Jul. 20, 1993, which is a continuation-in-part of U.S. application Ser. No. 08/005,229, filed Jan. 15, 1993, now U.S. Pat. No. 5,338,872, and a continuation-in-part of U.S. application Ser. No. 08/034,247, filed Mar. 22, 1993, now U.S. Pat. No. 5,430,160, which is a continuation-in-part application of U.S. application Ser. No. 07/949,107 filed Sep. 22, 1992, now abandoned, which is a continuation-in-part application of U.S. application Ser. No. 07/863,849, filed Apr. 6, 1992, now abandoned, which is a continuation-in-part application of U.S. application Ser. No. 07/862,955, filed Apr. 3, 1992, now abandoned, which is a continuation-in-part application of U.S. application Ser. No. 07/763,805, filed Sep. 23, 1991, now abandoned. This application is also a 371 of PCT/US94/00499.

This invention was made with Government support under NIH Grant #CA 42031 and NIH Grant #CA 55131 awarded by the National Institutes of Health. The Government has certain rights in the invention.

BACKGROUND OF THE INVENTION

The present invention relates to a process for preparing 10-desacetoxytaxol, 10-desacetoxybaccatin III and derivatives of 10-desacetoxytaxol and 10-desacetoxybaccatin III.

Taxol is a natural product extracted from the bark of yew trees. It has been shown to have excellent antitumor activity in in vivo animal models, and recent studies have elucidated its unique mode of action, which involves abnormal polymerization of tubulin and disruption of mitosis. It is currently undergoing clinical trials against ovarian, breast and other types of cancer in the United States and France and preliminary results have confirmed it as a most promising chemotherapeutic agent. The structure of taxol and the numbering system conventionally used is shown below; this numbering system is also applicable to compounds used in the process of the present invention.

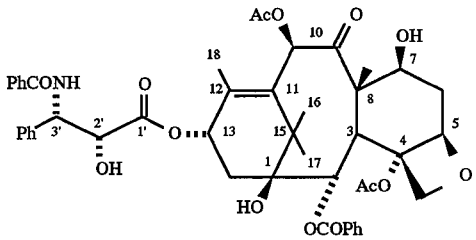

In Colin U.S. Pat. No. 4,814,470, it was reported that a taxol derivative, commonly referred to as taxotere, has an activity significantly greater than taxol. Taxotere has the following structure:

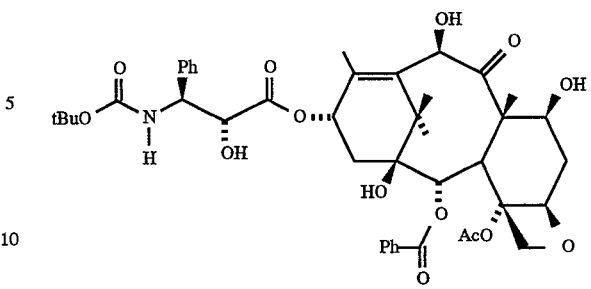

Although taxol and taxotere are promising chemotherapeutic agents, a need remains for additional chemotherapeutic agents. The tetracyclic core of taxol bears a C10 acetoxy substituent and taxotere bears a C10 hydroxy substituent which, if modified, would lead to the preparation of a series of taxol analogs. To date, however, the selective manipulation of the C10 acetoxy and hydroxy groups has presented a formidable problem.

SUMMARY OF THE INVENTION

Among the objects of the present invention, therefore, is the provision of an improved process for preparing 10-desacetoxytaxol, 10-desoxytaxotere, 10-desacetoxybaccatin III and derivatives of 10-desacetoxytaxol and 10-desacetoxybaccatin III.

Briefly, therefore, the present invention is directed to a process for the preparation of 10-desacetoxy and 10-desoxy taxanes. According to this process, a taxane having a C10 leaving group such as hydroxy, acyloxy or sulfonyloxy is reacted with samarium diiodide. The C10 leaving group is selectively and nearly quantitatively removed from the taxane.

Other objects and features of this invention will be in part apparent and in part pointed out hereinafter.

DETAILED DESCRIPTION OF THE INVENTION

As used herein "Ar" means aryl; "Ph" means phenyl; "Ac" means acetyl; "Et" means ethyl; "R" means alkyl unless otherwise defined; "Bu" means butyl; "Pr" means propyl; "TES" means triethylsilyl; "TMS" means trimethylsilyl; "TPAP" means tetrapropylammonium perruthenate; "DMAP" means p-dimethylamino pyridine; "DMF" means dimethylformamide; "LDA" means lithium diisopropylamide; "LHMDS" means lithium hexamethyldisilazide; "LAH" means lithium aluminum hydride; "Red-Al" means sodium bis(2-methoxyethoxy) aluminum hydride; "AIBN" means azo-(bis)-isobutyronitrile; "10-DAB" means 10-desacetylbaccatin III; FAR means 2-chloro-1,1,2-trifluorotriethylamine; protected hydroxy means —OR wherein R is a hydroxy protecting group; sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; and "hydroxy protecting group" includes, but is not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein, either alone or with the various substituents defined herein are preferably lower alkyl containing from one to six carbon atoms in the principal chain and up to 15 carbon atoms. They may be substituted, straight, branched chain or cyclic and include methyl, ethyl, propyl, isopropyl, butyl, hexyl, cyclopropyl, cyclopentyl, cyclohexyl and the like.

The alkenyl groups described herein, either alone or with the various substituents defined herein are preferably lower alkenyl containing from two to six carbon atoms in the principal chain and up to 15 carbon atoms. They may be substituted, straight or branched chain and include ethenyl, propenyl, isopropenyl, butenyl, isobutenyl, hexenyl, and the like.

The alkynyl groups described herein, either alone or with the various substituents defined herein are preferably lower alkynyl containing from two to six carbon atoms in the principal chain and up to 15 carbon atoms. They may be substituted, straight or branched chain and include ethynyl, propynyl, butynyl, isobutynyl, hexynyl, and the like.

The aryl moieties described herein, either alone or with various substituents, contain from 6 to 15 carbon atoms and include phenyl. Substituents include alkanoxy, protected hydroxy, halogen, alkyl, aryl, alkenyl, acyl, acyloxy, nitro, amino, amido, etc. Phenyl is the more preferred aryl.

The heteroaryl moieties described herein, either alone or with various substituents, contain from 5 to 15 atoms and include, furyl, thienyl, pyridyl and the like. Substituents include alkanoxy, protected hydroxy, halogen, alkyl, aryl, alkenyl, acyl, acyloxy, nitro, amino, and amido.

The acyloxy groups described herein contain alkyl, alkenyl, alkynyl, aryl or heteroaryl groups.

The sulfonyloxy groups described herein contain alkyl, alkenyl, alkynyl, aryl or heteroaryl groups.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

Surprisingly, it has been discovered that taxanes possessing C10 hydroxy, acyloxy such as acetoxy or sulfonyloxy substituents may be selectively and nearly quantitatively converted to the corresponding 10-desacetoxy or 10-desoxytaxane. The C10 hydroxy, acyloxy or sulfonyloxy substituted taxane may have a tricyclic or tetracyclic core and corresponds to the formula:

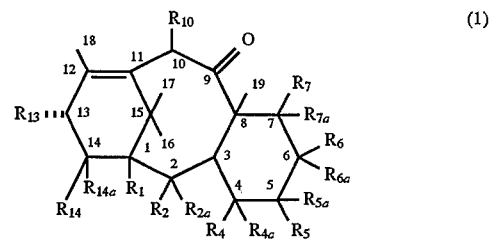

(1)

wherein $R_1$ is hydrogen, hydroxy, protected hydroxy or together with $R_{14}$ forms a carbonate;

$R_2$ is hydrogen, hydroxy, —$OCOR_{31}$, or together with $R_{2a}$ forms an oxo;

$R_{2a}$ is hydrogen or together with $R_2$ forms an oxo;

$R_4$ is hydrogen, together with $R_{4a}$ forms an oxo, oxirane or methylene, or together with $R_{5a}$ and the carbon atoms to which they are attached form an oxetane ring;

$R_{4a}$ is hydrogen, alkyl, alkenyl, alkynyl, aryl, heteroaryl, cyano, hydroxy, —$OCOR_{30}$, or together with $R_4$ forms an oxo, oxirane or methylene;

$R_5$ is hydrogen or together with $R_{5a}$ forms an oxo;

$R_{5a}$ is hydrogen, hydroxy, protected hydroxy, acyloxy, together with $R_5$ forms an oxo, or together with $R_4$ and the carbon atoms to which they are attached form an oxetane ring;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo;

$R_{7a}$ is hydrogen, halogen, protected hydroxy, —$OR_{28}$, or together with $R_7$ forms an oxo;

$R_{10}$ is hydroxy, acyloxy or sulfonyloxy;

$R_{13}$ is hydroxy, protected hydroxy or

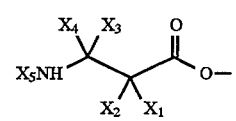

$R_{14}$ is hydrogen, alkyl, alkenyl, alkynyl, aryl, or heteroaryl, hydroxy, protected hydroxy or together with $R_1$ forms a carbonate;

$R_{14a}$ is hydrogen, alkyl, alkenyl, alkynyl, aryl, or heteroaryl;

$R_{28}$ is hydrogen, acyl, hydroxy protecting group or a functional group which increases the solubility of the taxane derivative;

$R_{29}$, $R_{30}$ and $R_{31}$ are independently hydrogen, alkyl, alkenyl, alkynyl, monocyclic aryl or monocyclic heteroaryl;

$X_1$ is —$OX_6$, —$SX_7$, or —$NX_8X_9$;

$X_2$ is hydrogen, alkyl, alkenyl, alkynyl, aryl, or heteroaryl;

$X_3$ and $X_4$ are independently hydrogen, alkyl, alkenyl, alkynyl, aryl, or heteroaryl;

$X_5$ is —$COX_{10}$, —$COOX_{10}$, —$COSX_{10}$, —$CONX_8X_{10}$, or —$SO_2X_{11}$;

$X_6$ is hydrogen, alkyl, alkenyl, alkynyl, aryl, heteroaryl, hydroxy protecting group, or a functional group which increases the water solubility of the taxane derivative;

$X_7$ is alkyl, alkenyl, alkynyl, aryl, heteroaryl, or sulfhydryl protecting group;

$X_8$ is hydrogen, alkyl, alkenyl, alkynyl, aryl, heteroaryl, or heterosubstituted alkyl, alkenyl, alkynyl, aryl or heteroaryl;

$X_9$ is an amino protecting group;

$X_{10}$ is alkyl, alkenyl, alkynyl, aryl, heteroaryl, or heterosubstituted alkyl, alkenyl alkynyl, aryl or heteroaryl;

$X_{11}$ is alkyl, alkenyl, alkynyl, aryl, heteroaryl, —$OX_{10}$, or —$NX_8X_{14}$; and $X_{14}$ is hydrogen, alkyl, alkenyl, alkynyl, aryl, or heteroaryl.

The reaction is illustrated in Reaction Scheme 1 wherein $R_1$–$R_{14a}$ are as previously defined. The reaction between the taxane and samarium diiodide may be carried out at a temperature between about –78° C. and 100° C., preferably at or below 0° C., in a solvent, for example, an ether such as tetrahydrofuran, a dipolar aprotic such as HMPA (hexamethylphosphoramide) or DMF (dimethylformamide), or combinations thereof. Advantageously, the samarium diiodide selectively abstracts the C10 leaving group; C13 side chains and other substituents on the nucleus remain undisturbed.

REACTION SCHEME 1

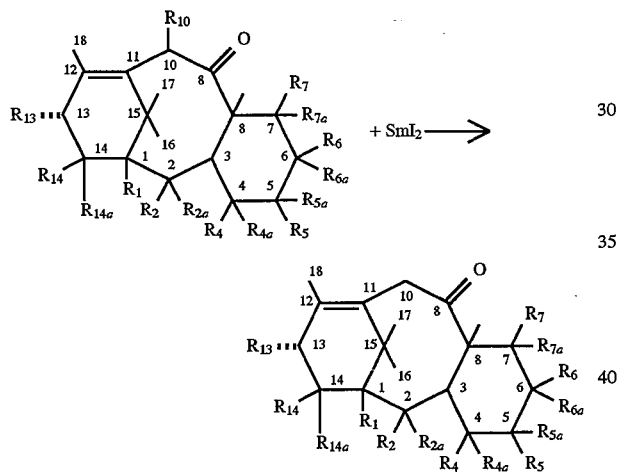

Preferably, the C10 hydroxy, acyloxy or sulfonyloxy substituted taxane is tetracyclic and corresponds to the formula

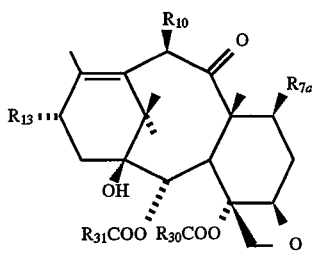

wherein $R_{7a}$ is hydrogen, hydroxy, protected hydroxy or —$OR_{28}$;

$R_{10}$ is hydroxy or acetoxy;

$R_{13}$ is hydroxy, protected hydroxy or

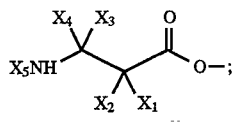

$R_{28}$ is acyl;

$R_{30}$ is alkyl;

$R_{31}$ is monocyclic aryl; and $X_1$–$X_5$ are as previously defined.

Most preferably, the taxane is baccatin III, 10-desacetyl baccatin III, taxol, taxotere, or other biologically active taxane having a comparable C13 side chain. Baccatin III and 10-desacetyl baccatin III have the following structures.

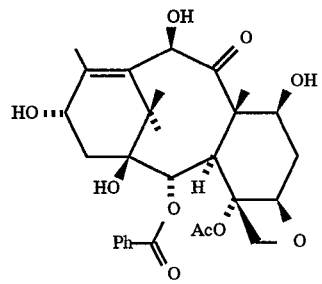

and

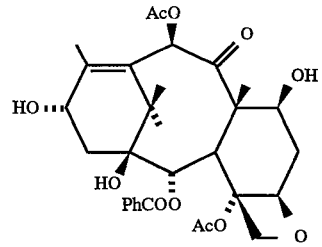

Baccatin III, 10-desacetyl baccatin III and taxol can be separated from mixtures extracted from natural sources such as the needles, stems, bark or heartwood of numerous Taxus species. Taxotere and other biologically active taxanes may be prepared semisynthetically from baccatin III and 10-desacetyl baccatin III as set forth in U.S. Pat. Nos. 4,924,011 and 4,924,012 or by the reaction of a β-lactam and an alkoxide having the taxane tricyclic or tetracyclic nucleus and a C13 metallic or ammonium oxide substituent. The β-lactams have the following structural formula:

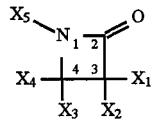

wherein $X_1$–$X_5$ are as defined above and the alkoxides have the formula:

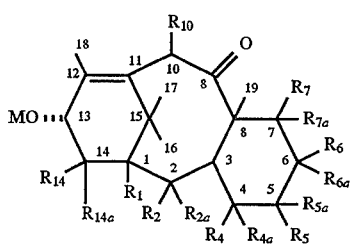

wherein $R_1$–$R_{14a}$ are as previously defined and M comprises ammonium or is a metal optionally selected from the group comprising Group IA, Group IIA and transition metals, and preferably, Li, Mg, Na, K or Ti.

Taxanes having a C10 sulfonyloxy substitutent may be prepared by reacting 10-desacetyl baccatin III or other C10 hydroxy substituted taxane with a sulfonyl chloride such as methanesulfonylchloride, benzenesulfonylchloride or toluenesulfonylchloride and a tertiary amine.

Taxanes having C10 acyloxy substituents other than acetate can be prepared using 10-DAB as a starting material as illustrated in Reaction Scheme 2. 10-DAB may readily be protected with a variety of protecting groups at C7 with a silylchloride such as triethylsilylchloride or an acylating agent such as acetic anhydride to yield a 7-protected 10-DAB. The C10 hydroxy substituent of 7-protected 10-DAB 15 may then be readily acylated with any standard acylating agent to yield derivative 16 having a new C10 acyloxy substituent and, if desired, the C7 protecting group can readily be removed.

als. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride.

Baccatin III and 10-DAB analogs having different substituents at C2 and/or C4 can be prepared as set forth in Reaction Schemes 3–7. To simplify the description, 10-DAB-is used as the starting material. It should be understood, however, that baccatin III derivatives or analogs may be produced using the same series of reactions (except for the protection of the C10 hydroxy group) by simply replacing 10-DAB with baccatin III as the starting material. Derivatives of the baccatin III and 10-DAB analogs having different substituents at various positions, for instance C1, C2, C4, C7, and C13, can then be prepared by carrying out any of the other reactions described herein and any others which are within the level of skill in the art.

In Reaction Scheme 3, protected 10-DAB 3 is converted to the triol 18 with lithium aluminum hydride. Triol 18 is then converted to the corresponding C4 ester using $Cl_2CO$ in pyridine followed by a nucleophilic agent (e.g., Grignard reagents or alkyllithium reagents).

REACTION SCHEME 2

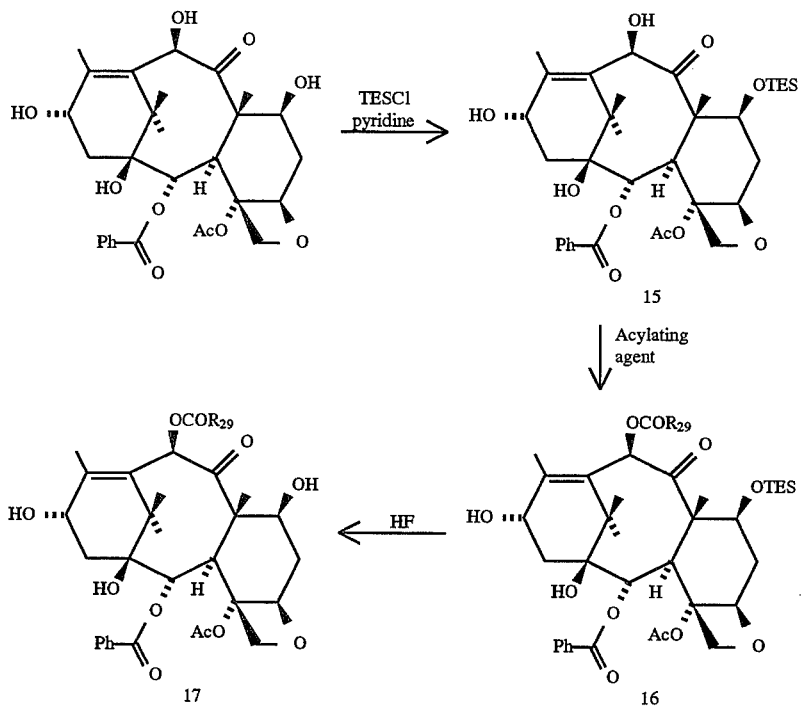

Taxanes having alternative C2 and/or C4 esters can be prepared using baccatin III and 10-DAB as starting materi- Scheme 3

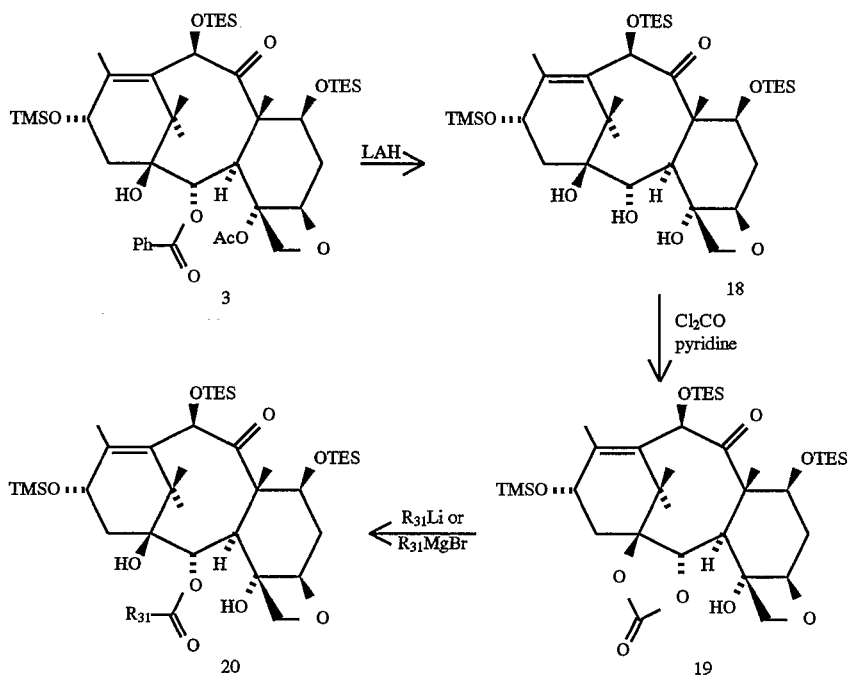

Deprotonation of triol 18 with LDA followed by introduction of an acid chloride selectively gives the C4 ester. For example, when acetyl chloride was used, triol 18 was converted to 1,2 diol 4 as set forth in Reaction Scheme 4.

Triol 18 can also readily be converted to the 1,2 carbonate 19. Acetylation of carbonate 19 under vigorous standard conditions provides carbonate 21 as described in Reaction Scheme 5; addition of alkyllithiums or Grignard reagents to carbonate 19 provides the C2 ester having a free hydroxyl group at C4 as set forth in Reaction Scheme 3.

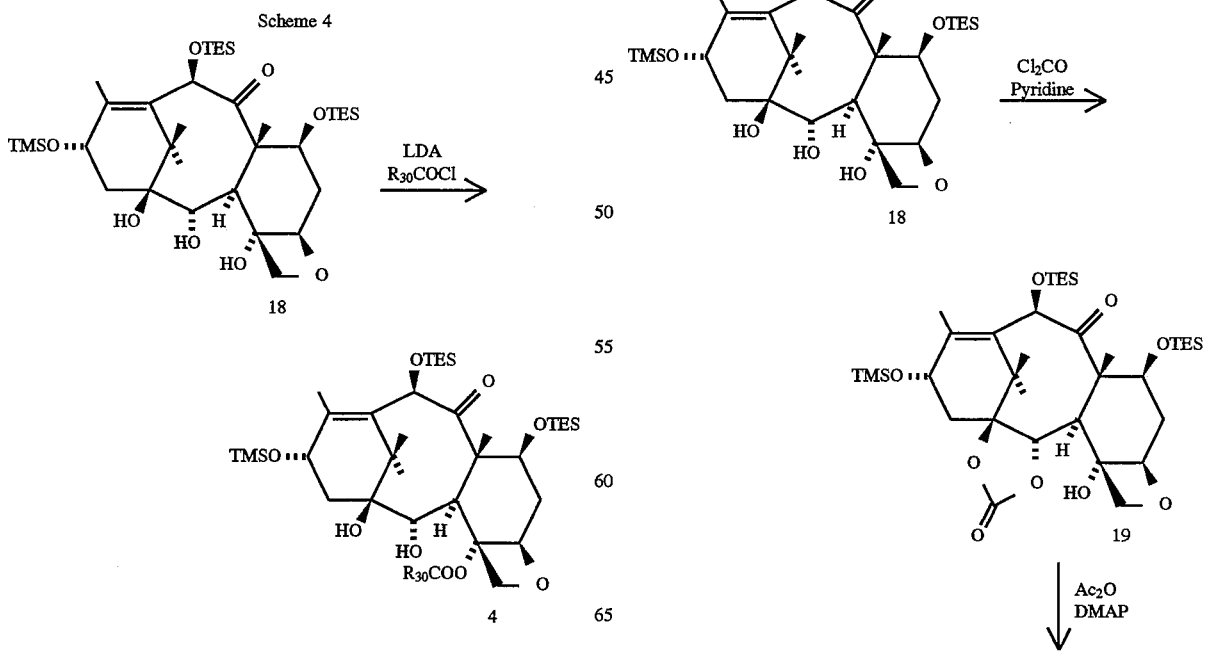

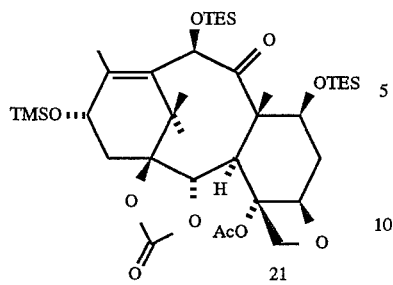

21

As set forth in Reaction Scheme 6, other C4 substituents can be provided by reacting carbonate 19 with an acid chloride and a tertiary amine to yield carbonate 22 which is then reacted with alkyllithiums or Grignard reagents to provide 10-DAB derivatives having new substituents at C2.

Scheme 6

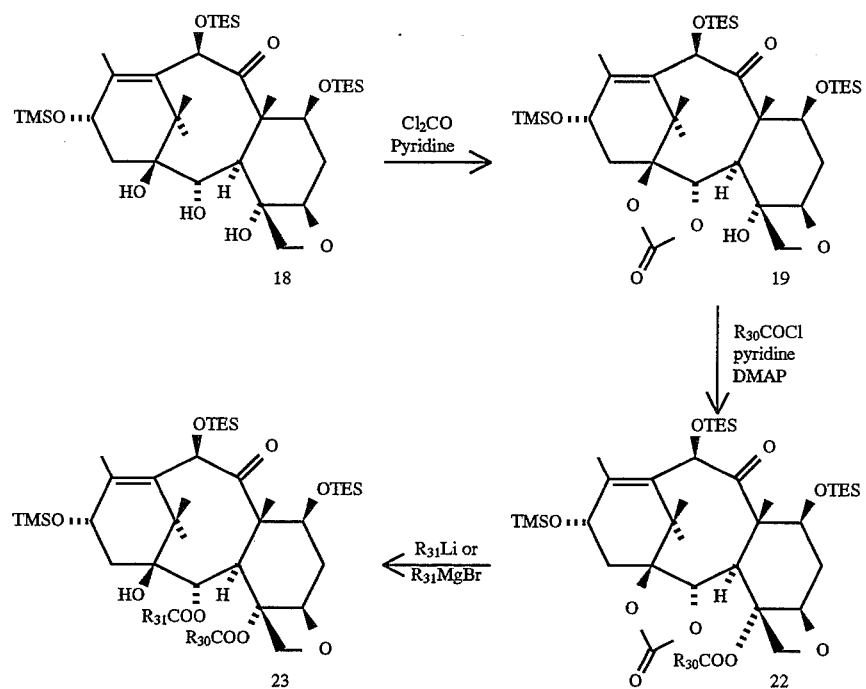

Alternatively, baccatin III may be used as a starting material and reacted as shown in Reaction Scheme 10. After being protected at C7 and C13, baccatin III is reduced with LAH to produce 1,2,4,10 tetraol 24. Tetraol 24 is converted to carbonate 25 using $Cl_2CO$ and pyridine, and carbonate 25 is acylated at C10 with an acid chloride and pyridine to produce carbonate 26 (as shown) or with acetic anhydride and pyridine (not shown). Acetylation of carbonate 26 under vigorous standard conditions provides carbonate 27 which is then reacted with alkyl lithiums to provide the baccatin III derivatives having new substituents at C2 and C10. The C10 sulfonyloxy analog may be prepared by reacting carbonate 25 with a sulfonylchloride instead of an acylating agent to produce a C10 sulfonyloxy analog of carbonate 26 and then proceeding as otherwise set forth in Reaction Scheme 10.

Scheme 7

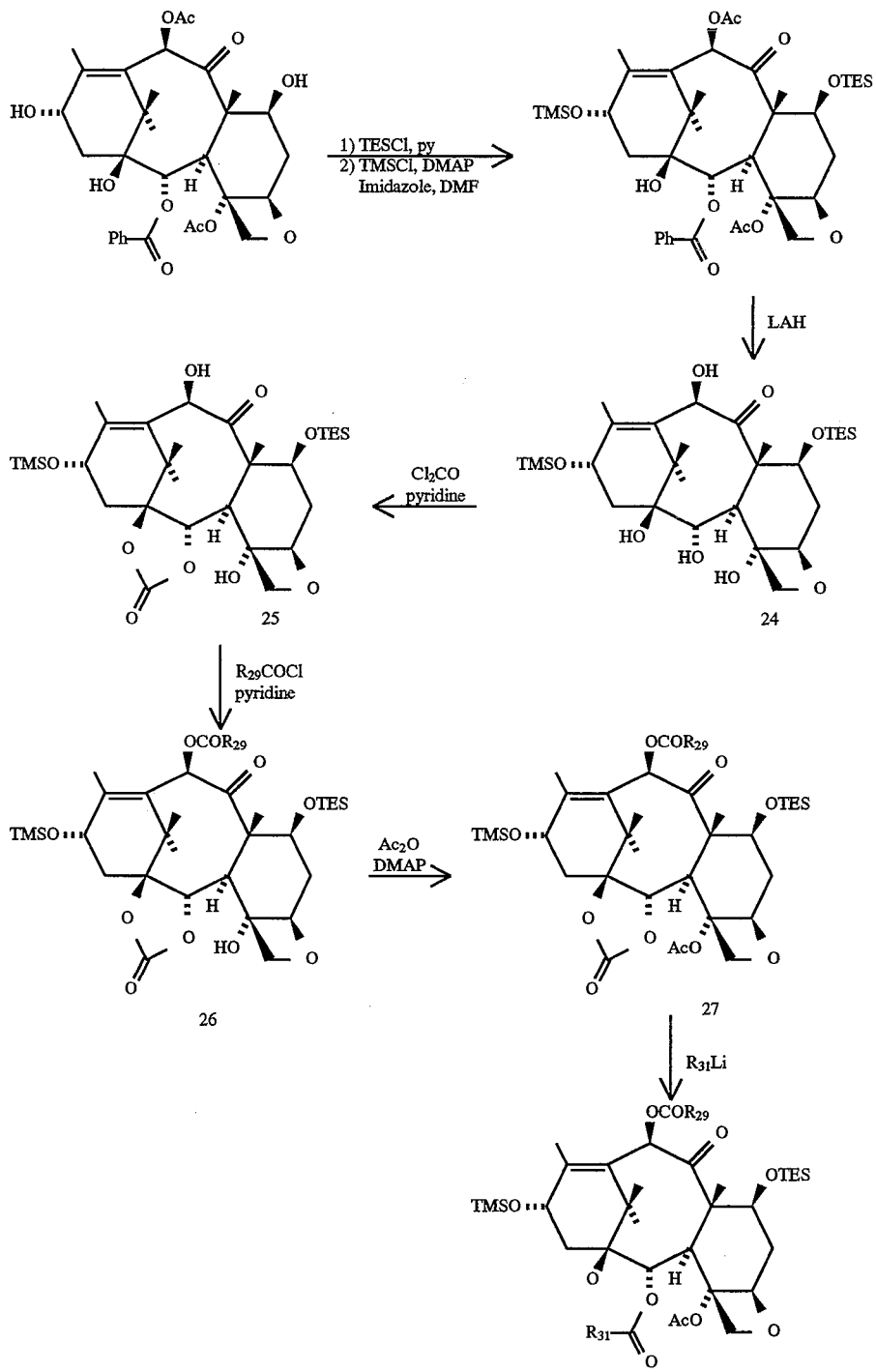

C7 dihydro and other C7 substituted taxanes can be prepared as set forth in Reaction Schemes 8 and 9.

As shown in Reaction Scheme 9, Baccatin III may be converted into 7-fluoro baccatin III by treatment with FAR at room temperature in THF solution. Other baccatin derivatives with a free C7 hydroxyl group behave similarly. Alternatively, 7-chloro baccatin III can be prepared by treatment of baccatin III with methane sulfonyl chloride and triethylamine in methylene chloride solution containing an excess of triethylamine hydrochloride.

REACTION SCHEME 8

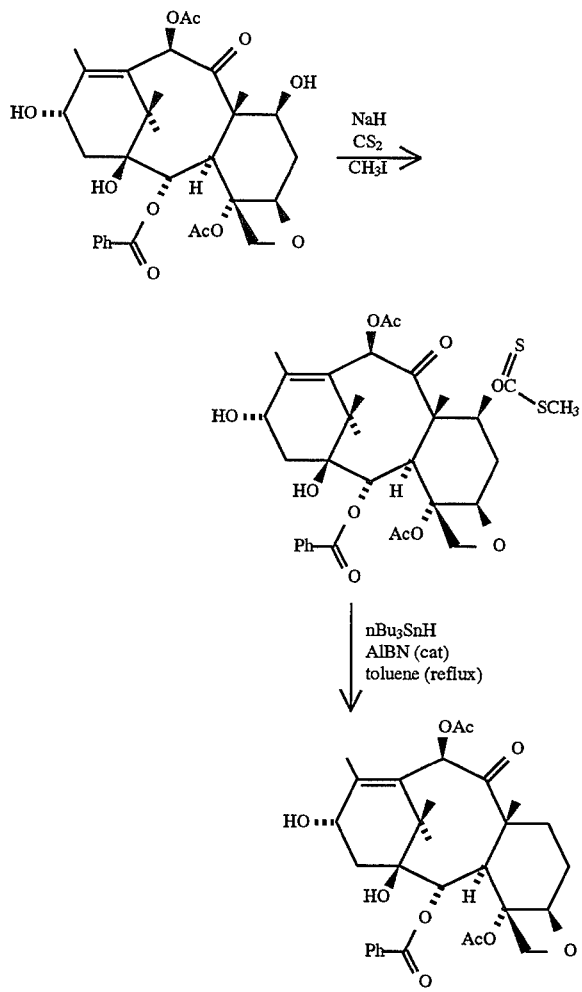

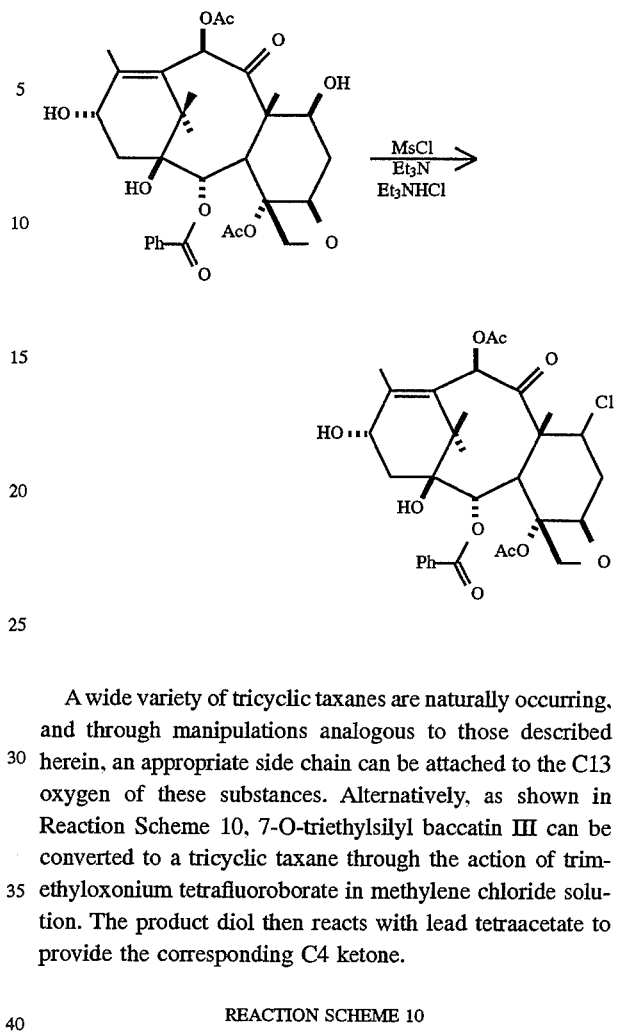

A wide variety of tricyclic taxanes are naturally occurring, and through manipulations analogous to those described herein, an appropriate side chain can be attached to the C13 oxygen of these substances. Alternatively, as shown in Reaction Scheme 10, 7-O-triethylsilyl baccatin III can be converted to a tricyclic taxane through the action of trimethyloxonium tetrafluoroborate in methylene chloride solution. The product diol then reacts with lead tetraacetate to provide the corresponding C4 ketone.

REACTION SCHEME 9

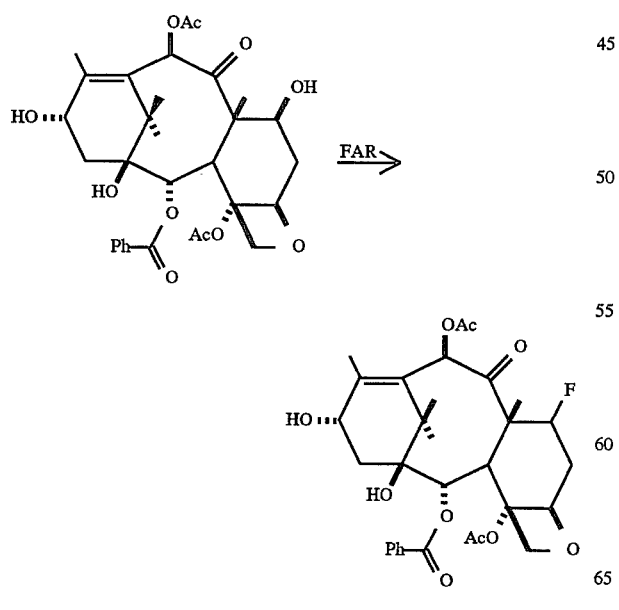

-continued

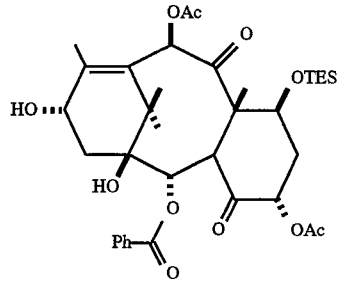

Recently a hydroxylated taxane (14-hydroxy-10-deacetylbaccatin III) has been discovered in an extract of yew needles (C&EN, p 36–37, Apr. 12, 1993). Derivatives of this hydroxylated taxane having the various C2, C4, etc. functional groups described above may also be prepared by using this hydroxylated taxane. In addition, the C14 hydroxy group together with the C1 hydroxy group of 10-DAB can be converted to a 1,2-carbonate as described in C&EN or it may be converted to a variety of esters or other functional groups as otherwise described herein in connection with the C2, C4, C7, C9, C10 and C13 substituents.

The following examples are provided to more fully illustrate the invention.

EXAMPLE 1

10-Desacetoxybaccatin III:

To a solution of baccatin III (20 mg; 0.034 mmol) in THF (0.09 mL) at 0° C. under nitrogen was added a solution of SmI$_2$ (0.1M; 0.9 mL; 0.09 mmol) in THF. After stirring 45 minutes at 0° C. the flask was opened to the air, and the reaction mixture diluted with ethyl acetate (10 mL). The mixture was poured into aqueous HCl (0.2N; 25 mL), extracted with ethyl acetate, and the extract was washed successively with saturated aqueous NaHCO$_3$ and brine, dried over Na$_2$SO$_4$ and evaporated. The product was isolated by flash chromatography (SiO$_2$; 80% ethyl acetatehexanes) affording 16.6 mg (92%) of 10-desacetoxybaccatin III which was recrystallized from CHCl$_3$-hexanes. mp 230°–232° C. [α]$^{25}$D=−103.6 (c=0.00195, CHCl$_3$). IR (cm$^{-1}$): 3100, 2970, 2950, 2900, 1750, 1710, 1460, 1370, 1320, 1270, 1255, 1110, 980, 890, 760, 700. $^1$H-nmr (500 MHz, CDCl$_3$) δ 8.11 (dd; 2H; J=8.4, 1.2 Hz; o-Bz); 7.61 (dt; 1H; J=7.5,1.2 Hz; p-Bz); 7.48 (br t; 2H; J=7.8 Hz; m-Bz); 5.66 (br d; 1H; J=6.9 Hz; H-2β); 4.98 (br dd; 1H; J=9.4,2; H-5α); 4.83 (br; 1H; w1/2 19 Hz; H-13β); 4.34 (dt; 1H; J=11.2, 7.8 Hz; H-7α); 4.31 (br d; 1H; J=8.4 Hz; H-20α); 4.17 (br d; 1H; J=6.9 Hz; H-3α); 4.15 (dd; 1H; J=8.4, 1 Hz; H-20β); 3.84 (d; 1H; J=15.6 Hz; H-10α); 3.46 (ddd; 1H; J=15.6,3.7,1.6 Hz; H-10β); 2.64 (ddd; 1H; J=14.4,9.4,6.9 Hz; H-6α); 2.29 (s; 3H; 4-OAc); 2.28 (m; 2H; H-14α and H-14β); 1.95 (t; 3H; J=1.6 Hz; 18-Me); 1.94 (d, 1H; J=6.8 Hz; 13-OH); 1.79 (ddd; 1H; J=14.4, 11.2, 2.1 Hz; H-6β); 1.64 (s; 3H; 19-Me); 1.58 (s; 1H; 1-OH); 1.38 (d; 1H; J=7.8 Hz; 7-OH); 1.13 (s, 3H; 16-Me); 1.06 (s, 3H; 17-Me).

EXAMPLE 2

7-Triethylsilyl-10-desacetoxybaccatin III:

To a stirred solution of 10-desacetoxybaccatin III (10.0 mg; 0.019 mmol) in anhydrous pyridine (0.05 mL) at room temperature and under nitrogen, triethylchlorosilane (15 L; 0.09 mmol) was added and the resulting mixture was stirred at room temperature for 48 h. After diluting with ethyl acetate (5 mL) the mixture was poured into saturated aqueous NaHCO$_3$ (25 mL) and extracted with ethyl acetate. The extract was washed successively with water, 10% aqueous CuSO$_4$ and brine, dried over Na$_2$SO$_4$ and evaporated. The product was purified by flash chromatography (SiO$_2$; 40% EA-hexanes) affording 11.1 mg (91%) of 7-triethylsilyl-10-desacetoxybaccatin III.

EXAMPLE 3

10-Desacetoxytaxol:

To a stirred solution of taxol (35 mg; 0.041 mmol) in THF (0.1 mL) at 0° C. under nitrogen was added a solution of SmI$_2$ (0.1M; 1.0 mL; 0.10 mmol) in THF. After stirring 45 minutes at 0° C. the flask was opened to the air and the reaction mixture diluted with ethyl acetate (10 mL). The mixture was poured into aqueous HCl (0.2N; 25 mL), extracted with ethyl acetate, and the extract was washed successively with saturated aqueous NaHCO$_3$ and brine, dried over Na$_2$SO$_4$ and evaporated. The product was isolated by flash chromatography (SiO$_2$; 80% ethyl acetatehexanes) affording 29.4 mg (90%) of 10-desacetoxytaxol.

EXAMPLE 4

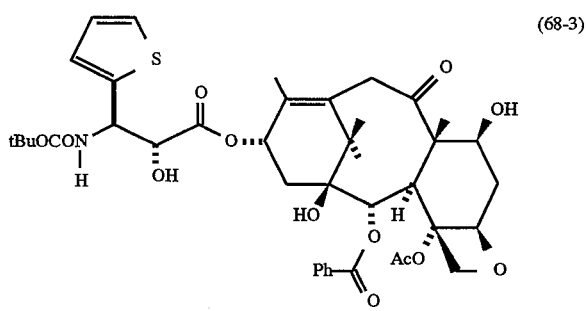

(68-3)

Preparation of 3'-desphenyl-3'-(2-thienyl)-N-desbenzoyl-N-(t-butoxycarbonyl)-10-desacetoxy taxol.

To a solution of 7-O-triethylsilyl-10-desacetoxy baccatin (III) (47.5 mg, 0.073 mmol) in 0.7 mL of THF at −45° C. was added dropwise 0.08 mL of a 0.98M solution of LiN(SiMe$_3$)$_2$ in hexane. After 0.5 h at −45° C., a solution of cis-1-t-butoxycarbonyl-3-triethylsilyloxy-4-(2-thienyl)-azetidin-2-one (70.0 mg, 0.182 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 64.3 mg of a mixture containing (2'R,3'S)-2', 7-(bis)-O-triethylsilyl-3'-desphenyl-3'-(2-thienyl)-N-desbenzoyl-N-(t-butoxycarbonyl)-10-desacetoxy taxol and a small amount of the (2'S,3'R) isomer.

To a solution of 64.3 mg (0.056 mmol) of the mixture obtained from the previous reaction in 3.2 mL of acetonitrile and 0.15 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 46.3 mg of material which was purified by flash chromatography to give 40.1 mg (91%) of 3'-desphenyl-3'-(2-thienyl)-N-desbenzoyl-N-(t-butoxycarbonyl)-10-desacetoxy taxol, which was recrystallized from methanol/water.

m.p.158°–160° C.; $[\alpha]^{25}$Na –58,4° (c 0.0028, CHCl$_3$). $^1$H NMR (CDCl$_3$, 300 MHz) δ 8.11(d, J=6.9 Hz, 2H, benzoate ortho), 7.61(m, 1H, benzoate para), 7.50(m, 2H, benzoate meta), 7.27(dd, J=5.5, 1.2 Hz, 1H, thienyl), 7.06(d, J=3.3 Hz, 1H, thienyl), 7.01(dd, J=5.7, 3.9 Hz, 1H, thienyl), 6.13(td, J=6.3, 0.9 Hz, 1H, H13), 5.70(d, J=6.9 Hz, 1H, H2), 5.49(d, J=9.2 Hz, 1H, NH), 5.34(d, J=9.9 Hz, 1H, H3'), 4.62(dd, J=5.4 2.1 Hz, 1H, H5), 4.30(d, J=8.1 Hz, 1H, H20α), 4.29(s, 1H, H2'), 4.17(d, J=8.1 Hz, 1H, H20β), 4.06(d, J=6.9 Hz, 1H, H7), 3.81(d, J=15.3 Hz, H10α), 3.51(d, J=6.6 Hz, 1H, H3), 3.41(m, 1H, 2'OH), 2.61(m, 1H, H6α), 2.36(s, 3H, 4Ac), 2.30(m, 1H, H10β), 2.17(br s, 1H, 7 OH), 2.06(m, 1H, H14α), 1.81(m, 1H, H14β), 1.76(br s, 3H, Me18), 1.66(s, 1H, 1 OH), 1.62(m, 1H, H6β), 1.35(s, 9H, 3Me t-buthoxy), 1.25(s, 3H, Me17), 1.19(s, 3H, Me19), 1.17(s, 3H, Me16).

EXAMPLE 5

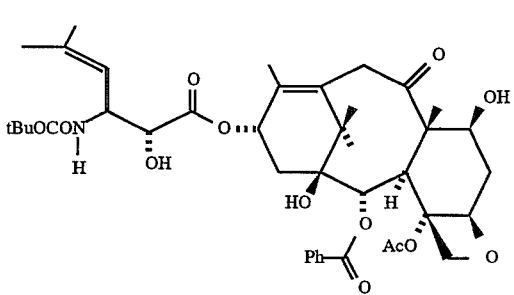

(68-4)

Preparation of 3'-desphenyl-3'-(isobutenyl)-N-desbenzoyl-N-(t-butoxycarbonyl)-10-desacetoxy taxol.

To a solution of 7-O-triethylsilyl-10-desacetoxy baccatin (III) (50.0 mg, 0.077 mmol) in 0.8 mL of THF at –45° C. was added dropwise 0.09 mL of a 0.98M solution of LiN(SiMe$_3$)$_2$ in hexane. After 0.5 h at –45° C., a solution of cis-1-t-butoxycarbonyl-3-(2-methoxyisopropyloxy)-4-(isobutenyl)azetidin-2-one (58.0 mg, 0.193 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 62.7 mg of a mixture containing (2'R,3'S)-2'-O-(2-methoxyisopropyl)-7O-triethylsilyl-3'-desphenyl-3'-(isobutenyl)-N-desbenzoyl-N-(t-butoxycarbonyl)-10-desacetoxy taxol and a small amount of the (2'S,3'R) isomer.

To a solution of 62.7 mg (0.059 mmol) of the mixture obtained from the previous reaction in 3.5 mL of acetonitrile and 0.16 mL of pyridine at 0° C. was added 0.55 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 51.5 mg of material which was purified by flash chromatography to give 43.0 mg (95%) of 3'-desphenyl-3'-(isobutenyl)-N-desbenzoyl-N-(t-butoxycarbonyl)-10-desacetoxy taxol, which was recrystallized from methanol/water.

m.p.153°–155° C.; $[\alpha]^{25}$Na–56.3° (c 0.003, CHCl$_3$). $^1$H NMR (CDCl$_3$, 300 MHz) δ 8.10(d, J=7.3 Hz, 2H, benzoate ortho), 7.60(m, 1H, benzoate para), 7.47(m, 2H, benzoate meta), 6.15(td, J=8.5, 1.8 Hz, 1H, H13), 5.69(d, J=6.9 Hz, 1H, H2), 5.32(d, J=9.2 Hz, 1H, NH), 4.93(dd, J=9.6, 1.8 Hz, 1H, H5), 4.82(d, J=8.7 Hz, 1H, Me$_2$C=C$\underline{H}$—), 4.76(td, J=8.7, 2.7 Hz, 1H, H3'), 4.37(d, J=8.7 Hz, 1H, H20α), 4.22(d, J=8.7 Hz, 1H, H20β), 4.18(d, J=2.7 Hz, 1H, H2'), 4.03(d, J=7.3 Hz, 1H, H7), 3.82(d, J=15.2 Hz, 1H, H10α), 3.47(m, 1H, 2'OH), 3.41(d, J=6.6 Hz, 1H, H3), 2.60(m, 1H, H6α), 2.39(m, 1H, H10β), 2.37(s, 3H, 4Ac), 2.18(s, 1H, 7 OH), 2.08(m, 1H, H14α), 1.78(m, 1H, H14β), 1.76(s, 3H, Me18), 1.74(s, 6H, 2Me from isobuthenyl), 1.63(m, 1H, H6β), 1.36(s, 9H, 3Me t-buthoxy) 1.26(s, 3H, Me17), 1.18 (s, 3H, Me19), 1.15(s, 3H, Me16).

EXAMPLE 6

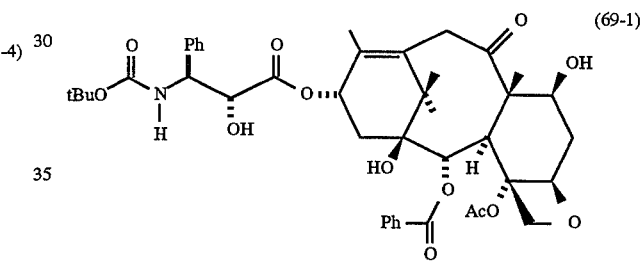

(69-1)

Preparation of N-desbenzoyl-N-(t-butoxycarbonyl)-10-desacetoxy taxol.

To a solution of 7-O-triethylsilyl-10-desacetoxy baccatin (III) (50.0 mg, 0.077 mmol) in 0.8 mL of THF at –45° C. was added dropwise 0.09 mL of a 0.98M solution of LiN(SiMe$_3$)$_2$ in hexane. After 0.5 h at –45° C., a solution of cis-1-t-butoxycarbonyl-3-triethylsiloxy-4-phenylazetidin-2-one (67.5 mg, 0.193 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 72.0 mg of a mixture containing (2'R,3'S)-2', 7-(bis) -O-triethylsilyl-N-desbenzoyl-N-(t-butoxycarbonyl)-10-desacetoxy taxol and a small amount of the (2'S,3'R) isomer.

To a solution of 72.0 mg (0.071 mmol) of the mixture obtained from the previous reaction in 3.8 mL of acetonitrile and 0.17 mL of pyridine at 0° C. was added 0.60 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 57.4 mg of material which was purified by flash chromatography to give 39.4 mg (71%) of N-desbenzoyl-N-(t-butoxycarbonyl)-10-desactoxy taxol, which was recrystallized from methanol/water.

m.p.145°–147° C.; $[\alpha]^{25}$Na–54.4° (c 0.0027, CHCl$_3$). $^1$H NMR (CDCl$_3$, 300 MHz) δ 8.11(d, J=7.1 Hz, 2H, benzoate ortho), 7.61–7.23 (m, 8H, benzoate, phenyl), 6.13 (td, J=6.3, 0.9 Hz, 1H, H13), 5.68(d, J=6.9 Hz, 1H, H2), 5.43(d, J=9.2 Hz, 1H, NH), 5.26(d, J=9.9 Hz, 1H, H3'), 4.96(dd, J=5.4 2.1 Hz, 1H, H5), 4.31(d, J=8.1 Hz, 1H, H20α), 4.22(s, 1H, H2'), 4.18(d, J=8.1 Hz, 1H, H20β), 4.03(d, J=6.9 Hz, 1H, H7), 3.81(d, J=15.1 Hz, H10α), 3.43(m, 1H, 2'OH), 3.40(d, J=6.6 Hz, 1H, H3), 2.60(m, 1H, H6α), 2.38(s, 3H, 4Ac), 2.32(m, 1H, H10β), 2.15(br s, 1H, 7 OH), 2.09(m, 1H, H14α), 1.83(m, 1H, H14β), 1.78(br s, 3H, Me18), 1.66(s, 1H, 1 OH), 1.63(m, 1H, H6β), 1.36(s, 9H, 3Me t-butoxy), 1.25(s, 3H, Me17), 1.18(s, 3H, Me19), 1.16 (s, 3H, Me16).

EXAMPLE 7

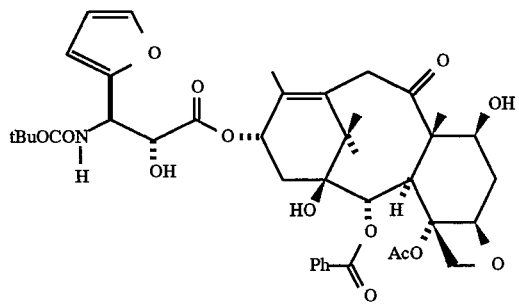

(69-2)

Preparation of 3'-desphenyl-3'-(2-furyl)-N-desbenzoyl-N-(t-butoxycarbonyl)-10-desacetoxy taxol.

To a solution of 7-O-triethylsilyl-10-desacetoxy baccatin (III) (50.0 mg, 0.077 mmol) in 0.8 mL of THF at –45° C. was added dropwise 0.09 mL of a 0.98M solution of LiN(SiMe$_3$)$_2$ in hexane. After 0.5 h at –45° C., a solution of cis-1-t-butoxycarbonyl-3-triethylsiloxy-4-(2-furyl)azetidin-2-one (72.8 mg, 0.195 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 69.4 mg of a mixture containing (2'R, 3'S)-2',7-(bis)-O-triethylsilyl-3'-desphenyl-3'-(2-furyl)-N-desbenzoyl-N-(t-butoxy-carbonyl)-10-desacetoxy taxol and a small amount of the (2'S,3'R) isomer.

To a solution of 69.4 mg (0.068 mmol) of the mixture obtained from the previous reaction in 3.8 mL of acetonitrile and 0.17 mL of pyridine at 0° C. was added 0.60 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 59.0 mg of material which was purified by flash chromatography to give 41.0 mg (76%) of 3'-desphenyl-3'-(2-furyl)-N-desbenzoyl-N-(t-butoxycarbonyl)-10-desacetoxy taxol, which was recrystallized from methanol/water.

m.p.151°–153° C.; $[\alpha]^{25}$Na–56.5° (c 0.0025, CHCl$_3$). $^1$H NMR (CDCl$_3$, 300 MHz) δ 8.11(d, J=7.3 Hz, 2H, benzoate ortho), 7.60(m, 1H, benzoate para), 7.49(m, 2H, benzoate meta), 7.41(m, 1H, furyl), 6.37(m, 1H, furyl), 6.34(m, 1H, furyl), 6.13(dd, J=6.3, 0.9 Hz, 1H, H13), 5.69(d, J=6.6 Hz, 1H, H2), 5.49(d, J=9.2 Hz, 1H, NH), 5.34(d, J=9.9 Hz, 1H, H3'), 4.62(dd, J=5.4, 2.1 Hz, 1H, H5), 4.30 (d, J=8.1 Hz, 1H, H20α), 4.29 (s, 1H, H2'), 4.17 (d, J=8.1 Hz, 1H, H20β), 4.06(d, J=6.9, 1H, H7), 3.81(d, J=15.3 Hz, 1H, H10α), 3.51(d, J=6.6 Hz, 1H, H3), 3.41(m, 1H, 2'OH), 2.61(m, 1H, H6α), 2.36(s, 3H, 4Ac), 2.32(m, 2H, H14α), 2.28(m, 1H, H10β), 2.17(br s, 1H, 7OH), 2.14(m, 1H, H14α), 1.82(m, 1H, H14β), 1.76(br s, 3H, Me18), 1.66(s, 1H, 1 OH), 1.62(m, 1H, H6β), 1.35(s, 9H, 3Me t-butoxy), 1.25(s, 3H, Me17), 1.19(s, 3H, Me19), 1.16(s, 3H, Me16).

EXAMPLE 8

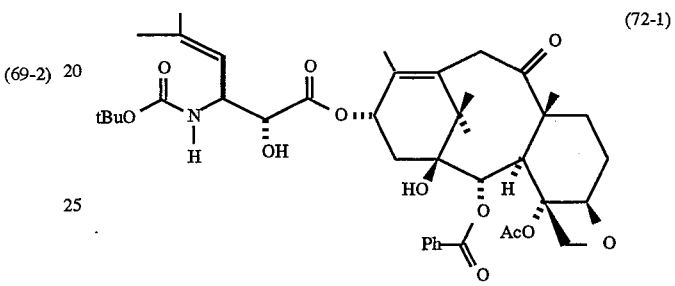

(72-1)

Preparation of 3'-desphenyl-3'-(isobutenyl)-N-desbenzoyl-N-(t-butoxycarbonyl)-7-deshydroxy-10-desacetoxy taxol.

To a solution of 7-deshydroxy-10-desacetoxy baccatin (III) (28.7 mg, 0.051 mmol) in 0.7 mL of THF at –45° C. was added dropwise 0.06 mL of a 0.98M solution of LiN(SiMe$_3$)$_2$ in hexane. After 0.5 h at –45° C., a solution of cis-1-t-butoxycarbonyl-3-(2-methoxyisopropyloxy)-4-(isobutenyl)azetidin-2-one (47.3 mg, 0.15 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 40.3 mg of a mixture containing (2'R,3'S)-2'-O-(2-methoxyisopropyl)-3'-desphenyl-3'-(isobutenyl)-N-debenzoyl-N-(t-butoxycarbonyl)-7-deshydroxy-10-desacetoxy taxol and a small amount of the (2'S,3'R) isomer.

To a solution of 40.3 mg (0.046 mmol) of the mixture obtained from the previous reaction in 3.2 mL of acetonitrile and 0.15 mL of pyridine at 0° C. was added 0.47 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 35.2 mg of material which was purified by flash chromatography to give 24.0 mg (70%) of 3'-desphenyl-3'-(isobutenyl)-N-debenzoyl-N-(t-butoxycarbonyl)-7-deshydroxy-10-desacetoxy taxol, which was recrystallized from methanol/water.

m.p.122°–125° C.; $[\alpha]^{25}$Na–64.3° (c 0.0025, CHCl$_3$). $^1$H NMR (CDCl$_3$, 300 MHz) δ 8.12(d, J=7.1 Hz, 2H, benzoate ortho), 7.60(m, 1H, benzoate para), 7.48(m, 2H, benzoate meta), 6.11(td, J=8.1, 1.8 Hz, 1H, H13), 5.68(d, J=6.9 Hz, 1H, H2), 5.23(d, J=9.9 Hz, 1H, NH), 5.12(d, J=9.9 Hz, 1H, H3'), 4.96(dd, J=9.1, 2.7 Hz, 1H, H5), 4.80(d, J=8.7 Hz, 1H, Me$_2$C=C$\underline{H}$—), 4.58(dd, J=5.7, 2.1 Hz, 1H, H2'), 4.30(d, J=8.1, 1H, H20α), 4.19(d, J=8.1 Hz, 1H, H20β), 3.97(d, J=6.9 Hz, H3), 3.83(d, J=16.5, 1H, H10α), 3.33(m, 1H, H10β), 3.30(m, 1H, 2'OH), 2.39(m, 1H, H14α), 2.35(s, 3H, 4Ac), 2.26(m, 1H, H14β), 2.19(m, 1H, H6α), 2.10(m, 1H, H7α), 1.95(m, 1H, H6β), 1.73(s, 3H, Me18), 1.69(s, 6H, 2Me from isobuthenyl), 1.63(s, 3H, Me19), 1.44(m, 1H, H7β), 1.39(br. s, 1H, 1 OH), 1.35(s, 9H, 3Me t-buthoxy), 1.25(s, 3H, Me16), 1.15(s, 3H, Me17).

EXAMPLE 9

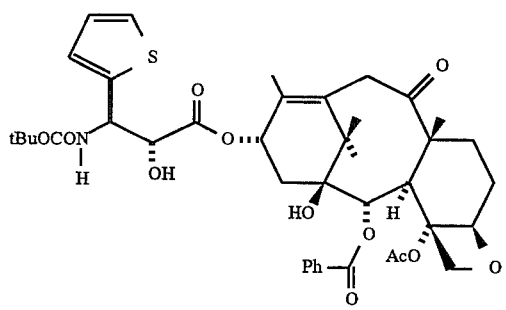

(72-2)

Preparation of 3'-desphenyl-3'-(2-thienyl)-N-desbenzoyl-N-(t-butoxycarbonyl)-7-deshydroxy-10-desacetoxy taxol.

To a solution of 7-deshydroxy-10-desacetoxy baccatin (III) (25.0 mg, 0.044 mmol) in 0.7 mL of THF at −45° C. was added dropwise 0.05 mL of a 0.98M solution of LiN(SiMe$_3$)$_2$ in hexane. After 0.5 h at −45° C., a solution of cis-1-t-butoxycarbonyl-3-triethylsilyloxy-4-(2-thienyl)-azetidin-2-one (50.0 mg, 0.13 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 35.4 mg of a mixture containing (2'R,3'S)-2'-O-triethylsilyl-3'-desphenyl-3'-(2-thienyl)-N-desbenzoyl-N-(t-butoxycarbonyl)-7-deshydroxy-10-desacetoxy taxol and a small amount of the (2'S,3'R) isomer.

To a solution of 35.4 mg (0.037 mmol) of the mixture obtained from the previous reaction in 3.2 mL of acetonitrile and 0.15 mL of pyridine at 0° C. was added 0.47 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 32.4 mg of material which was purified by flash chromatography to give 20.5 mg (71%) of 3'-desphenyl-3'-(2-thienyl)-N-desbenzoyl-N-(t-butoxycarbonyl)-7-deshydroxy-10-desacetoxy taxol, which was recrystallized from methanol/water.

m.p.132°–134° C.; [α]$^{25}$Na −61.3° (c 0.0025, CHCl$_3$). $^1$H NMR (CDCl$_3$, 300 MHz) δ 8.14(d, J=7.1 Hz, 2H, benzoate ortho), 7.61(m, 1H, benzoate para), 7.51 (m, 2H, benzoate meta), 7.29(dd, J=5.4, 1.2 Hz, 1H, thienyl), 7.09(d, J=3.3 Hz, 1H, thienyl), 7.01(dd, J=5.4, 3.3 Hz, 1H, thienyl), 6.14(td, J=8.4, 1.8 Hz, 1H, H13), 5.69(d, J=6.9 Hz, 1H, H2), 5.24(d, J=9.9 Hz, 1H, NH), 5.19(d, J=9.9 Hz, 1H, H3'), 4.93(dd, J=9.3, 2.7 Hz, 1H, H5), 4.62(dd, J=5.7, 2.1 Hz, 1H, H2'), 4.31(d, J=8.1, 1H, H20α), 4.21(d, J=8.1 Hz, 1H, H20β), 3.98(d, J=6.9 Hz, H3), 3.84(d, J=16.5, 1H, H10α), 3.38(m, 1H, H10β), 3.33(m, 1H, 2'OH), 2.40(m, 1H, H14α), 2.37(s, 3H, 4Ac), 2.27(m, 1H, H14β), 2.20(m, 1H, H6α), 2.11(m, 1H, H7α), 1.95(m, 1H, H6β), 1.74(s, 3H, Me18), 1.71(s, 3H, Me19), 1.46(m, 1H, H7β), 1.40(br. s, 1H, 1 OH), 1.34(s, 9H, 3Me t-buthoxy), 1.24(s, 3H, Me16), 1.13(s, 3H, Me17).

EXAMPLE 10

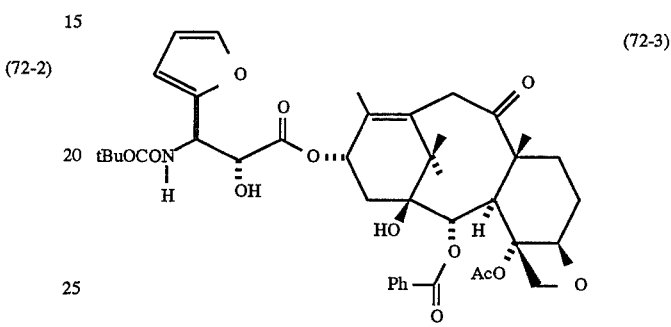

(72-3)

Preparation of 3'-desphenyl-3'-(2-furyl)-N-desbenzoyl-N-(t-butoxycarbonyl)-7-deshydroxy-10-desacetoxy taxol.

To a solution of 7-deshydroxy-10-desacetoxy baccatin (III) (35.0 mg, 0.061 mmol) in 0.8 mL of THF at −45° C. was added dropwise 0.07 mL of a 0.98M solution of LiN(SiMe$_3$)$_2$ in hexane. After 0.5 h at −45° C., a solution of cis-1-t-butoxycarbonyl-3-triethylsilyloxy-4-(2-furyl)-azetidin-2-one (68.0 mg, 0.18 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 56.3 mg of a mixture containing (2'R,3'S)-2'-O-triethylsilyl-3'-desphenyl-3'-(2-furyl)-N-desbenzoyl-N-(t-butoxycarbonyl)-7-deshydroxy-10-desacetoxy taxol and a small amount of the (2'S,3'R) isomer.

To a solution of 56.3 mg (0.06 mmol) of the mixture obtained from the previous reaction in 4.6 mL of acetonitrile and 0.22 mL of pyridine at 0° C. was added 0.68 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 48.3 mg of material which was purified by flash chromatography to give 31.7 mg (69%) of 3'-desphenyl-3'-(2-furyl)-N-desbenzoyl-N-(t-butoxycarbonyl)-7-deshydroxy-10-desacetoxy taxol, which was recrystallized from methanol/water.

m.p. 128°–131° C.; [α]$^{25}$Na −66.9° (c 0.0028, CHCl$_3$). $^1$H NMR (CDCl$_3$, 300 MHz) δ 8.13(d, J=6.9 Hz, 2H, benzoate ortho), 7.60(m, 1H, benzoate para), 7.48(m, 2H, benzoate meta), 7.40(m, 1H, furyl), 6.38(m, 1H, furyl), 6.32(m, 1H, furyl), 6.12(td, J=8.1, 1.8 Hz, 1H, H13), 5.67(d, J=6.9 Hz, 1H, H2), 5.22(d, J=9.9 Hz, 1H, NH), 5.17(d, J=9.9 Hz, 1H, H3'), 4.91(dd, J=9.1, 2.7 Hz, 1H, H5), 4.60(dd, J=5.7, 2.1 Hz, 1H, H2'), 4.28(d, J=8.1, 1H, H20α), 4.21(d, J=8.1 Hz, 1H, H20β), 3.95(d, J=6.9 Hz, H3), 3.82(d, J=16.5, 1H, H10α), 3.33(m, 1H, H10β), 3.31(m, 1H, 2'OH), 2.38(m, 1H, H14α), 2.35(s, 3H, 4Ac), 2.23(m, 1H, H14β), 2.20(m, 1H, H6α), 2.11(m, 1H, H7α), 1.94(m, 1H, H6β), 1.73(s, 3H, Me18), 1.71(s, 3H, Me19), 1.43(m, 1H, H7β), 1.38(br. s, 1H, 1 OH), 1.32(s, 9H, 3Me t-buthoxy), 1.23(s, 3H, Me16), 1.12(s, 3H, Me17).

EXAMPLE 11

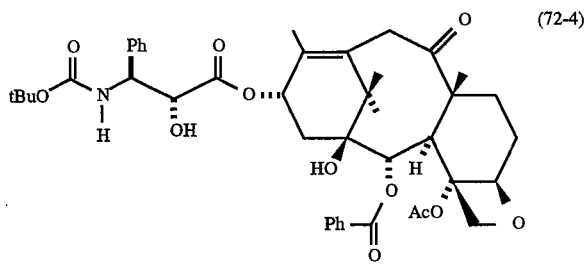

Preparation of N-desbenzoyl-N-(t-butoxycarbonyl)-7-deshydroxy-10-desacetoxy taxol.

To a solution of 7-deshydroxy-10-desacetoxy baccatin (III) (28.0 mg, 0.049 mmol) in 0.7 mL of THF at −45° C. was added dropwise 0.06 mL of a 0.98M solution of LiN(SiMe₃)₂ in hexane. After 0.5 h at −45° C., a solution of cis-1-t-butoxycarbonyl-3-triethylsilyloxy-4-(phenyl)-azetidin-2-one (56.0 mg, 0.15 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 38.4 mg of a mixture containing (2'R,3'S)-2'-O-triethylsilyl-N-desbenzoyl-N-(t-butoxycarbonyl)-7-deshydroxy-10-desacetoxy taxol and a small amount of the (2'S,3'R) isomer.

To a solution of 38.4 mg (0.041 mmol) of the mixture obtained from the previous reaction in 3.2 mL of acetonitrile and 0.15 mL of pyridine at 0° C. was added 0.46 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 33.8 mg of material which was purified by flash chromatography to give 27.4 mg (71%) of N-desbenzoyl-N-(t-butoxycarbonyl)-7-deshydroxy-10-desacetoxy taxol, which was recrystallized from methanol/water.

m.p.135°–138° C.; [α]²⁵Na−65.2° (c 0.0025, CHCl₃). ¹H NMR (CDCl₃, 300 MHz) δ 8.12(d, J=7.1 Hz, 2H, benzoate ortho), 7.60(m, 1H, benzoate para), 7.51(m, 2H, benzoate meta), 7.42–7.29(m, 5H, phenyl), 6.12(td, J=8.1, 1.8 Hz, 1H, H13), 5.66(d, J=6.9 Hz, 1H, H2), 5.21(d, J=9.9 Hz, 1H, NH), 5.16(d, J=9.9 Hz, 1H, H3'), 4.92(dd, J=9.1, 2.7 Hz, 1H, H5), 4.58(dd, J=5.7, 2.1 Hz, 1H, H2'), 4.30(d, J=8.1, 1H, H20α), 4.21(d, J=8.1 Hz, 1H, H20β), 3.97(d, J=6.9 Hz, H3),3.82(d, J=16.5, 1H, H10α), 3.41(m, 1H, H10β), 3.36(m, 1H, 2'OH), 2.40(m, 1H, H14α), 2.38(s, 3H, 4Ac), 2.26(m, 1H, H14β), 2.20(m, 1H, H6α), 2.13(m, 1H, H7α), 1.93(m, 1H, H6β), 1.73(s, 3H, Me18), 1.70(s, 3H, Me19), 1.43(m, 1H, H7β), 1.38(br. s, 1H, 1 OH), 1.32(s, 9H, 3Me t-buthoxy), 1.25(s, 3H, Me16), 1.15(s, 3H, Me17).

EXAMPLE 12

Taxanes 68-3, 68-4, 69-1, 69-2, 72-1, 72-2, 72-3, and 72-4 of Examples 4–11 were evaluated in in vitro cytotoxicity activity against human colon carcinoma cells HCT-116. Cytotoxicity was assessed in HCT116 cells by XTT (2,3-bis(2-methoxy-4-nitro-5-sulfophenyl)-5-[(phenylamino)carbonyl]-2H-tetrazolium hydroxide) assay (Scudiero et al, "Evaluation of a soluble tetrazolium/formazan assay for cell growth and drug sensitivity in culture using human and other tumor cell lines", Cancer Res. 48:4827–4833, 1988). Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an IC₅₀ which is the drug concentration required to inhibit cell proliferation (i.e. absorbance at 450 nm) to 50% of that of untreated control cells.

All compounds had an IC₅₀ less than 0.1, indicating that they are cytotoxically active.

What we claim is:

1. A process for abstracting a C10 hydroxy, acyloxy or sulfonyloxy substituent from a taxane comprising reacting the C10 hydroxy, acyloxy or sulfonyloxy substituted taxane with samarium diiodide.

2. The process of claim 1 wherein the taxane corresponds to the formula:

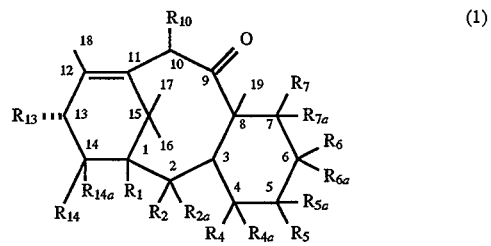

wherein

R₁ is hydrogen, hydroxy, protected hydroxy or together with R₁₄ forms a carbonate;

R₂ is hydrogen, hydroxy, —OCOR₃₁, or together with R₂ₐ forms an oxo;

R₂ₐ is hydrogen or together with R₂ forms an oxo;

R₄ is hydrogen, together with R₄ₐ forms an oxo, oxirane or methylene, or together with R₅ₐ and the carbon atoms to which they are attached form an oxetane ring;

R₄ₐ is hydrogen, alkyl, alkenyl, alkynyl, aryl, heteroaryl, cyano, hydroxy, —OCOR₃₀, or together with R₄ forms an oxo, oxirane or methylene;

R₅ is hydrogen or together with R₅ₐ forms an oxo;

R₅ₐ is hydrogen, hydroxy, protected hydroxy, acyloxy, together with R₅ forms an oxo, or together with R₄ and the carbon atoms to which they are attached form an oxetane ring;

$R_6$ is hydrogen, alkyl, alkenyl, alkynyl, aryl, or heteroaryl, hydroxy, protected hydroxy or together with $R_{6a}$ a forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo;

$R_{7a}$ is hydrogen, halogen, protected hydroxy, —$OR_{28}$, or together with $R_7$ forms an oxo;

$R_{10}$ is hydroxy, acyloxy or sulfonyloxy;

$R_{13}$ is hydroxy, protected hydroxy or

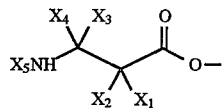

$R_{14}$ is hydrogen, alkyl, alkenyl, alkynyl, aryl, or heteroaryl, hydroxy, protected hydroxy or together with $R_1$ forms a carbonate;

$R_{14a}$ is hydrogen, alkyl, alkenyl, alkynyl, aryl, or heteroaryl;

$R_{28}$ is hydrogen, acyl, or a functional group which increases the solubility of the taxane derivative;

$R_{30}$ and $R_{31}$ are independently hydrogen, alkyl, alkenyl, alkynyl, monocyclic aryl or monocyclic heteroaryl;

$X_1$ is —$OX_6$, —$SX_7$, or —$NX_8X_9$;

$X_2$ is hydrogen, alkyl, alkenyl, alkynyl, aryl, or heteroaryl;

$X_3$ and $X_4$ are independently hydrogen, alkyl, alkenyl, alkynyl, aryl, or heteroaryl;

$X_5$ is —$COX_{10}$, —$COOX_{10}$, —$COSX_{10}$, —$CONX_8X_{10}$, or —$SO_2X_{11}$;

$X_6$ is hydrogen, alkyl, alkenyl, alkynyl, aryl, heteroaryl, hydroxy-protecting group, or a functional group which increases the water solubility of the taxane derivative;

$X_7$ is alkyl, alkenyl, alkynyl, aryl, heteroaryl, or sulfhydryl protecting group;

$X_8$ is hydrogen, alkyl, alkenyl, alkynyl, aryl, heteroaryl, or heterosubstituted alkyl, alkenyl, alkynyl, aryl or heteroaryl;

$X_9$ is an amino protecting group;

$X_{10}$ is alkyl, alkenyl, alkynyl, aryl, heteroaryl, or heterosubstituted alkyl, alkenyl alkynyl, aryl or heteroaryl;

$X_{11}$ is alkyl, alkenyl, alkynyl, aryl, heteroaryl, —$OX_{10}$, or —$NX_8X_{14}$; and $X_{14}$ is hydrogen, alkyl, alkenyl, alkynyl, aryl, or heteroaryl.

3. The process of claim 2 wherein the taxane has a C10 hydroxy substituent.

4. The process of claim 1 wherein the taxane has a C10 hydroxy substituent.

5. The process of claim 2 wherein the taxane has a C10 acetoxy substituent.

6. The process of claim 1 wherein the taxane has a C10 acetoxy substituent.

7. The process of claim 1 wherein the taxane has the formula

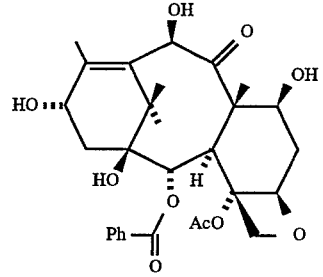

or

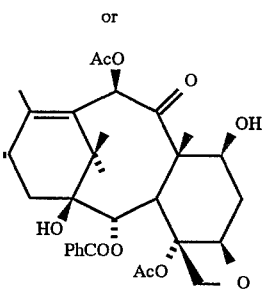

wherein Ac is acetyl and Ph is phenyl.

8. The process of claim 1 wherein the taxane has the formula

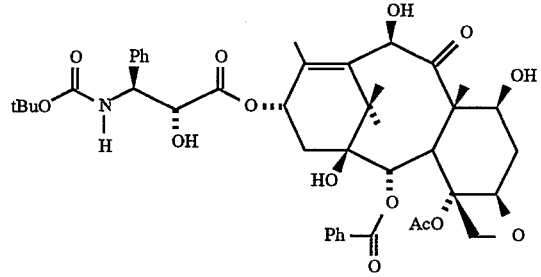

or

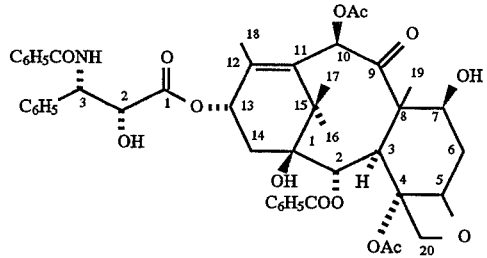

wherein Ac is acetyl, Ph is phenyl, and tBu is tert-butyl.

9. The process of claim 2 wherein the taxane has the formula

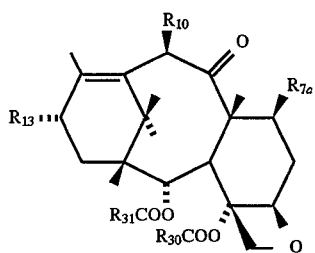
wherein
R$_{7a}$ is hydrogen, hydroxy, protected hydroxy or —OR$_{28}$;
R$_{10}$ is hydroxy or acetoxy;
R$_{13}$ is hydroxy, protected hydroxy or
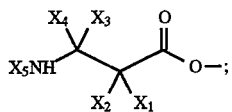
R$_{28}$ is acyl;
R$_{30}$ is alkyl;
R$_{31}$ is monocyclic aryl; and
X$_1$–X$_5$ are as defined in claim 2.
* * * * *